(12) United States Patent
Ilan

(10) Patent No.: US 10,980,866 B2
(45) Date of Patent: Apr. 20, 2021

(54) ALPHA-1 ANTI-TRYPSIN FOR TREATING LIVER DISEASES

(71) Applicant: Hadasit Medical Research Services and Development Ltd., Jerusalem (IL)

(72) Inventor: Yaron Ilan, Kfar-Tavor (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 32 days.

(21) Appl. No.: 15/507,383

(22) PCT Filed: Sep. 21, 2015

(86) PCT No.: PCT/IL2015/050962
§ 371 (c)(1),
(2) Date: Feb. 28, 2017

(87) PCT Pub. No.: WO2016/046822
PCT Pub. Date: Mar. 31, 2016

(65) Prior Publication Data
US 2017/0281739 A1 Oct. 5, 2017

Related U.S. Application Data

(60) Provisional application No. 62/053,267, filed on Sep. 22, 2014.

(51) Int. Cl.
*A61K 38/57* (2006.01)
*A61P 1/16* (2006.01)

(52) U.S. Cl.
CPC .............. *A61K 38/57* (2013.01); *A61P 1/16* (2018.01)

(58) Field of Classification Search
CPC ................................ A61K 38/57; A61P 1/16
See application file for complete search history.

(56) References Cited

U.S. PATENT DOCUMENTS

| | | | |
|---|---|---|---|
| 2009/0220518 A1 | 9/2009 | Dinarello et al. | |
| 2010/0111940 A1 * | 5/2010 | Flier | A61P 3/00 424/133.1 |
| 2011/0319330 A1 | 12/2011 | Shapiro | |
| 2013/0251671 A1 | 9/2013 | Kaufman et al. | |

FOREIGN PATENT DOCUMENTS

| | | | |
|---|---|---|---|
| WO | WO 2010/088415 | 8/2010 | |
| WO | WO 2013/128381 | 9/2013 | |
| WO | WO-2014106846 A2 * | 7/2014 | ....... A61K 47/48215 |
| WO | WO 2016/046822 | 3/2016 | |

OTHER PUBLICATIONS

Sigma Aldrich, α1-Antitrypsin from human plasma, catalog, A9024 S, accessed on Aug. 7, 2019.*
UniProt Protein Database, UniProtKB—P01009, Alpha-1-antitrypsin, accessed on Aug. 8, 2019.*
Brian Lam, Treatment options for nonalcoholic fatty liver disease, Ther Adv Gastroenterol (2010) 3(2) 121137.*
Giforkids (nonalcoholic fatty liver disease, https://giforkids.com/nonalcoholic-fatty-liver-disease/, published online Apr. 2012.*
Virginie Mansuy-Aubert, Imbalance between Neutrophil Elastase and its Inhibitor a1-Antitrypsin in Obesity Alters Insulin Sensitivity, Inflammation, and Energy Expenditure, Cell Metabolism 17, 534-548, Apr. 2, 2013.*
Supplementary European Search Report and the European Search Opinion dated Mar. 20, 2018 From the European Patent Office Re. Application No. 15843904.2. (8 Pages).
Wanner et al. "Novel Therapeutic Uses of Alpha-1 Antitrypsin: A Window to the Future", Journal of Chronic Obstructive Pulmonary Disease, COPS, XP009176323, 9(6): 583-588, Dec. 1, 2012.
International Preliminary Report on Patentability dated Apr. 6, 2017 From the International Bureau of WIPO Re. Application No. PCT/IL2015/050962.
International Search Report and the Written Opinion dated Jan. 18, 2016 From the International Searching Authority Re. Application No. PCT/IL2015/050962.
Guttman et al. "Acute-Phase Protein Alpha1-Anti-Trypsin: Diverting Injurious Innate and Adaptive Immune Responses From Non-Authentic Threats", Clinical and Experimental Immunology, 179(2): 161-172, Feb. 2015.
Hunt et al. "Alpha 1 Anti-Trypsin: One Protein, Many Functions", Current Molecular Medicine, 12(7): 827-835, Aug. 2012.
Jedicke et al. "Alpha-1-Antitrypsin Inhibits Acute Liver Failure in Mice", Hepatology, 59(6): 2299-2308, Available Online Apr. 28, 2014. Fig.4.
Blakolmer et al. "Chronic Liver Allograft Rejection in a Population Treated Primarily With Tacrolimus as Baseline Immunosuppression: Long-Term Follow-Up and Evaluation of Features for Histopathological Staging", Transplantation, 69(11): 2330-2336, Jun. 15, 2000.
Demetris et al. "Update of the International Banff Schema for Liver Allograft Rejection: Working Recommendations for the Histopathologic Staging and Reporting of Chronic Rejection", Hepatology, 31(3): 792-799, Mar. 2000.
Communication Pursuant to Article 94(3) EPC dated Nov. 29, 2018 From the European Patent Office Re. Application No. 15843904.2. (3 Pages).

* cited by examiner

Primary Examiner — James H Alstrum-Acevedo
Assistant Examiner — Erinne R Dabkowski

(57) ABSTRACT

Methods of treating liver diseases are provided. Accordingly there is provided a method of treating a liver disease selected from the group consisting of fatty liver disease and chronic liver rejection in a subject in need thereof, wherein said liver disease is not associated with genetic alpha-1 anti-trypsin (AAT) deficiency, the method comprising administering to the subject a therapeutically effective amount of AAT.

15 Claims, 7 Drawing Sheets
(1 of 7 Drawing Sheet(s) Filed in Color)
Specification includes a Sequence Listing.

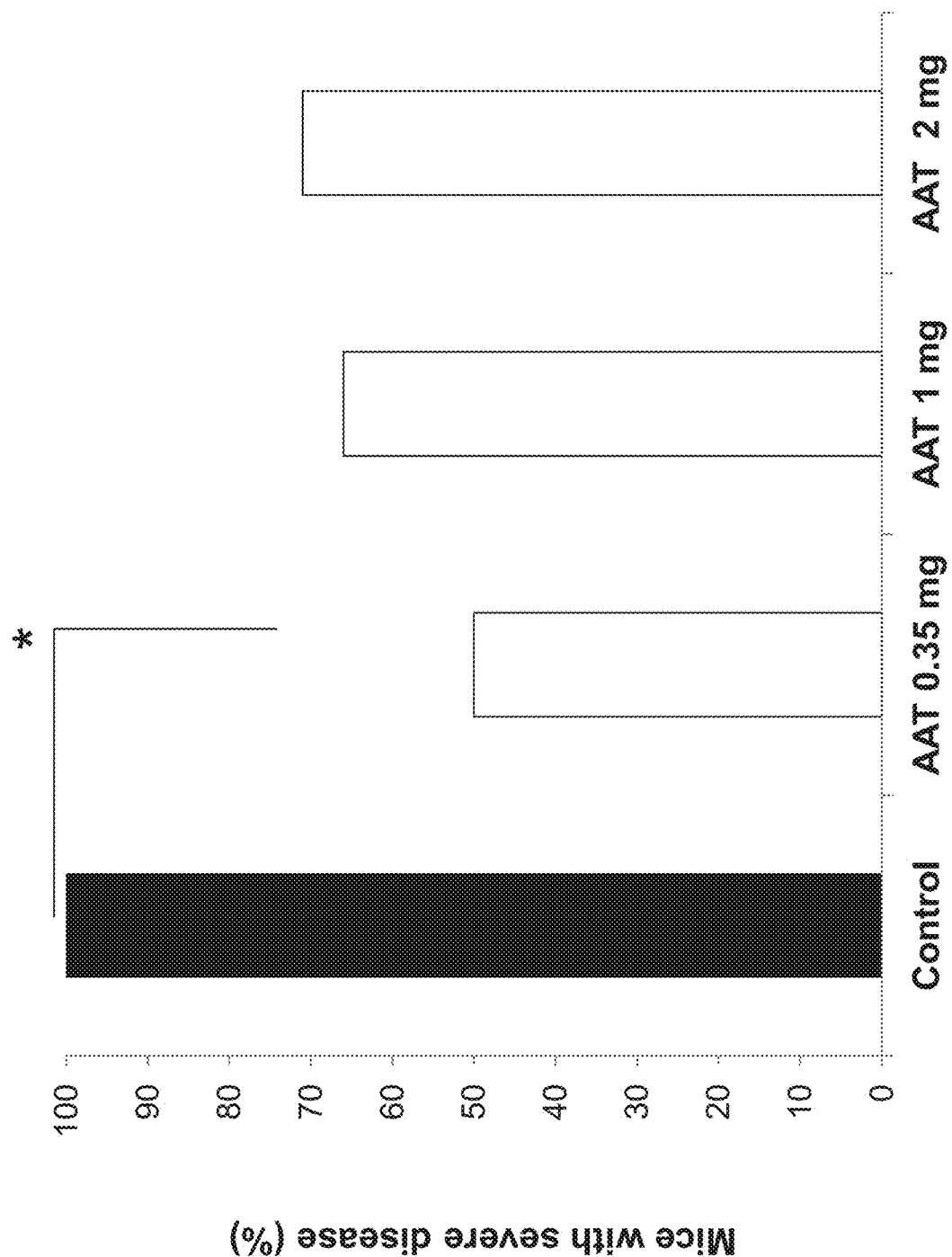

ALPHA-1 ANTI-TRYPSIN FOR TREATING LIVER DISEASES

RELATED APPLICATIONS

This application is a National Phase of PCT Patent Application No. PCT/IL2015/050962 having International filing date of Sep. 21, 2015, which claims the benefit of priority under 35 USC § 119(e) of U.S. Provisional Patent Application No. 62/053,267 filed on Sep. 22, 2014. The contents of the above applications are all incorporated by reference as if fully set forth herein in their entirety.

SEQUENCE LISTING STATEMENT

The ASCII file, entitled 69088SequenceListing.txt, created on Feb. 28, 2017, comprising 8,205 bytes, submitted concurrently with the filing of this application is incorporated herein by reference.

FIELD AND BACKGROUND OF THE INVENTION

The present invention, in some embodiments thereof, relates to methods of treating liver diseases and, more particularly, but not exclusively, to the use of alpha-1 anti-trypsin (AAT) in the treatment of fatty liver disease and/or chronic liver rejection.

Alcoholic and non alcoholic fatty liver disease (also known as hepatosteatosis) is a prevalent liver condition that occurs when lipids accumulate in liver cells. The accumulation of lipids causes cellular injury, sensitization of the liver to further injuries and damage to the hepatic microvascular circulation. The etiology of fatty liver disease is associated with excessive alcohol consumption, metabolic disorders, dietary conditions, exposure to certain chemicals and medications and complications of pregnancy (e.g., preeclampsia).

Fatty liver disease is a major health burden worldwide. The prevalence of non-alcoholic fatty liver disease (NAFLD) ranges from 15% to 37% of the population and is considered the most common liver disease worldwide. Moreover, NAFLD is also believed to affect as many as 3-10% of obese children. NAFLD can progress to a more advanced liver disease such as nonalcoholic steatohepatitis (NASH), a condition characterized by liver inflammation and damage, often accompanied by fibrosis or cirrhosis of the liver which can further lead to end stage liver disease and primary liver cancer. NASH has a prevalence of 3-10% of the general population.

Currently, there are no approved treatments for NAFLD and NASH which efficacy has been demonstrated by large-scale rigorous clinical trials. In general, current therapies include healthy lifestyle and non-specific metabolic modulators.

Chronic liver transplant rejection is a process which occurs over time, typically several months to years following engraftment, even in the presence of successful immunosuppression. While there have been improvements in the management of acute transplant rejection over the last thirty years as seen in the increased survival of transplants during the first year following the procedure, the half-life for long term organ survival has not improved and only about 50% of the transplants are functional at ten years.

To date, there are no therapeutic regimens which can effectively inhibit the chronic liver rejection process.

Alpha-1 anti-trypsin is a serine protease inhibitor (serpin) which inhibits a wide variety of proteases and protects the cells from proteolytic enzymes. The protein was called "anti-trypsin" because of its ability to covalently bind and irreversibly inactivate the enzyme trypsin in-vitro. AAT is synthesized in the liver and secreted into plasma, where it has a half life of approximately six days. Normal plasma concentration of AAT ranges from 1.3 to 3.5 mg/ml. However, under certain conditions AAT can behave as an acute phase reactant and its concentration increases 3-4-fold during host response to inflammation, tissue injury and/or distinct change such as acute infection and tumors. AAT easily diffuses into tissue spaces and forms a complex with target proteases, principally neutrophil elastase, which breaks down the connective tissue fiber elastin. Other enzymes such as trypsin, chymotrypsin, cathepsin G, plasmin, thrombin, tissue kallikrein, and factor Xa can also serve as substrates for AAT. The enzyme/inhibitor complex is then removed from the circulation by binding to serpin-enzyme complex (SEC) receptor and catabolized by the liver and spleen.

Beyond its anti-protease activity functions, AAT has been shown to play roles in processes such as immune-modulation, inflammation, proteostasis, necrosis and apoptosis [Hunt et al. Curr Mol Med (2012); 12:827-35]. Mutations in the AAT gene (SERPINA1) that lead to a deficiency in AAT are associated with respiratory complications such as emphysema and chronic obstructive pulmonary disease (COPD). AAT treatment has been disclosed in a number of indications including AAT deficiency, diabetes, allo- and xeno-transplantation, autoimmune diseases and cancer [see e.g. Guttman et al. Clin Exp Immunol. (2015) 179(2):161-72].

Additional background art includes:
Jedicke et al. Hepatology (2014) 59: 2299-2308;
US Patent Application Publication No: US 20130251671;
US Patent Application Publication No: 20110319330;
US Patent Application Publication No: US 20100111940;
International Patent Application Publication No: WO2013128381; and
International Patent Application Publication No: WO 2010088415.

SUMMARY OF THE INVENTION

According to an aspect of some embodiments of the present invention there is provided a method of treating a liver disease selected from the group consisting of fatty liver disease and chronic liver rejection in a subject in need thereof, wherein said liver disease is not associated with genetic alpha-1 anti-trypsin (AAT) deficiency, the method comprising administering to the subject a therapeutically effective amount of AAT, thereby treating the liver disease in the subject.

According to an aspect of some embodiments of the present invention there is provided an alpha-1 anti-trypsin (AAT) for use in treating a liver disease selected from the group consisting of fatty liver disease and chronic liver rejection, wherein said liver disease is not associated with genetic AAT deficiency.

According to some embodiments of the invention, the fatty liver disease is a non-alcoholic fatty liver disease (NAFLD).

According to some embodiments of the invention, the fatty liver disease is a nonalcoholic steatohepatitis (NASH).

According to some embodiments of the invention, the fatty liver disease is an alcoholic fatty liver disease.

According to some embodiments of the invention, the liver disease is not associated with a disease selected from the group consisting of diabetes, obesity, hypertriglyceridemia, hypercholesterolemia and hypertension.

According to an aspect of some embodiments of the present invention there is provided a method of administering alpha 1 anti trypsin (AAT), in a biologically active form, to a subject in need thereof for liver protection.

According to some embodiments of the invention, the alpha 1 anti trypsin is administered orally, intravenously, subcutaneous, intrarectal, intradermal, or by inhaler for liver protection.

According to some embodiments of the invention, the disease is infectious, whether viral, bacterial, parasitic of fungal to the liver.

According to some embodiments of the invention, the disease is metabolic or immune mediated.

According to some embodiments of the invention, the disease is fatty liver disease or non alcoholic steatohepatitis.

According to some embodiments of the invention, the disease is hepatic encephalopathy, ADHD, metabolic syndrome, diabetes, both type 1 and type 2, atherosclerosis or chronic fatigue syndrome.

According to some embodiments of the invention, the disease is acute or chronic liver disease from any cause.

According to some embodiments of the invention, the medicine that causes liver intoxication is acetaminophen or any other drug that induces drug induced liver injury, or any other compound, including alcohol, or any type of food ingredient that can cause liver damage.

According to some embodiments of the invention, the disease is cholestatic liver disease, or graft versus host disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
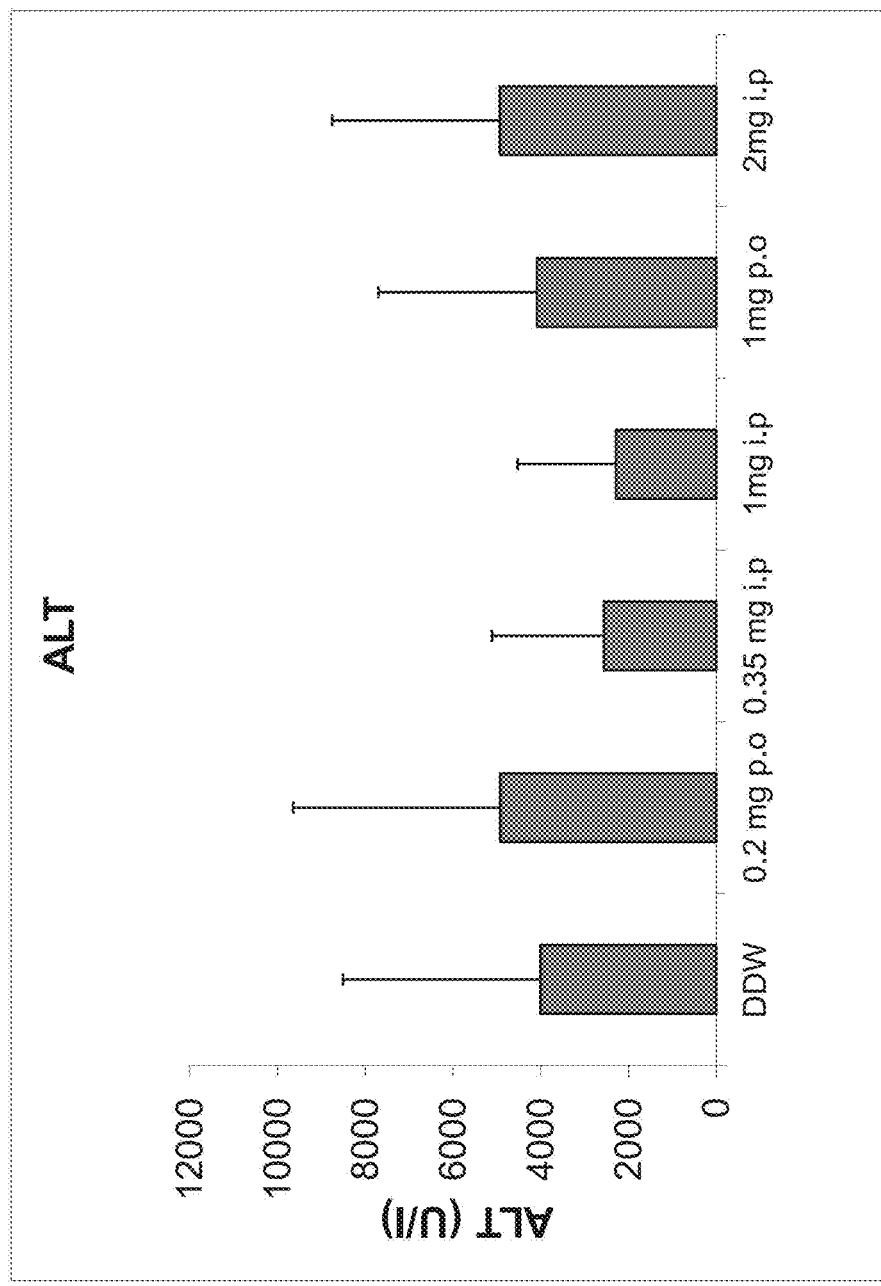
Figure 1B:
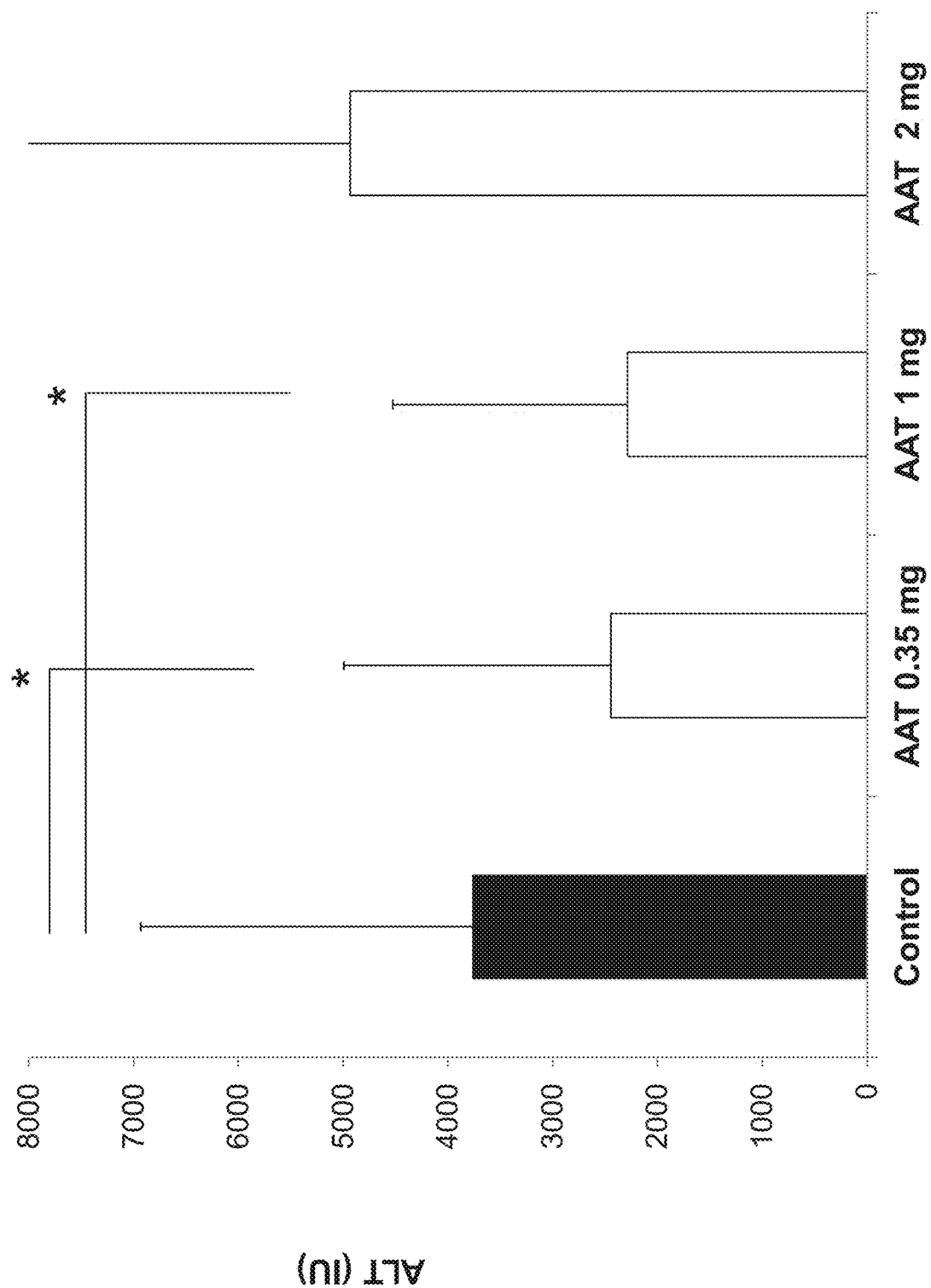

FIGS. 1A-C demonstrate the effect of alpha-1 anti-trypsin (AAT) treatment on alanine aminotransferase (ALT) serum levels in the concavalin A (ConA)-induced hepatitis mouse model, 15 hours following ConA administration. FIGS. 1A-B are graphs showing ALT serum levels in control (double distilled water, DDW) and AAT-treated mice in duplicate experiments. FIG. 1C is a graph showing the percentage of mice developing severe hepatitis as defined by serum ALT>1000 IU.

Figure 2:
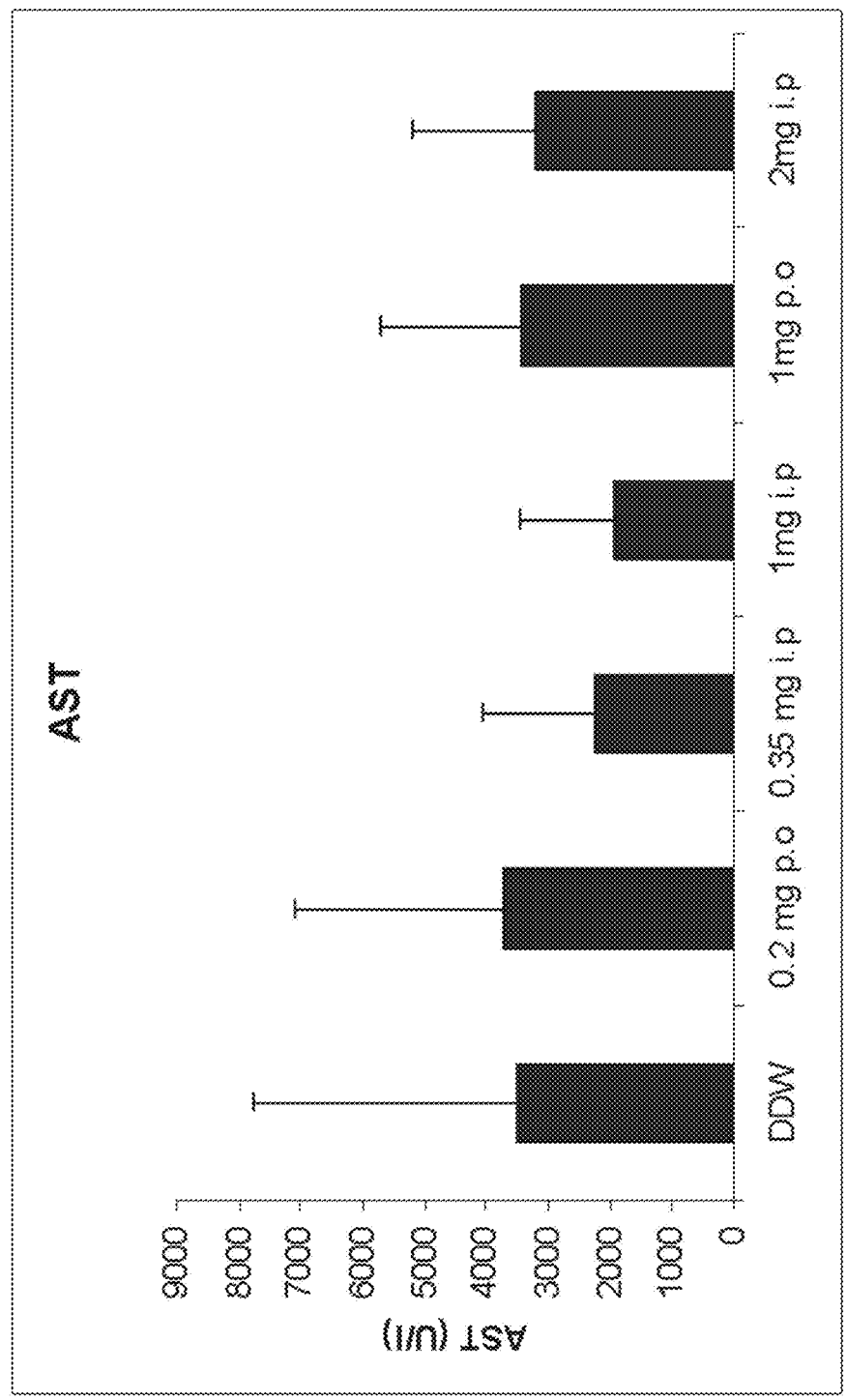

FIG. 2 is a graph of AST serum levels in control (DDW) and AAT-treated mice demonstrating the effect of AAT treatment on ALT serum levels in the in the ConA-induced hepatitis mouse model, 15 hours following ConA administration.

Figure 3:
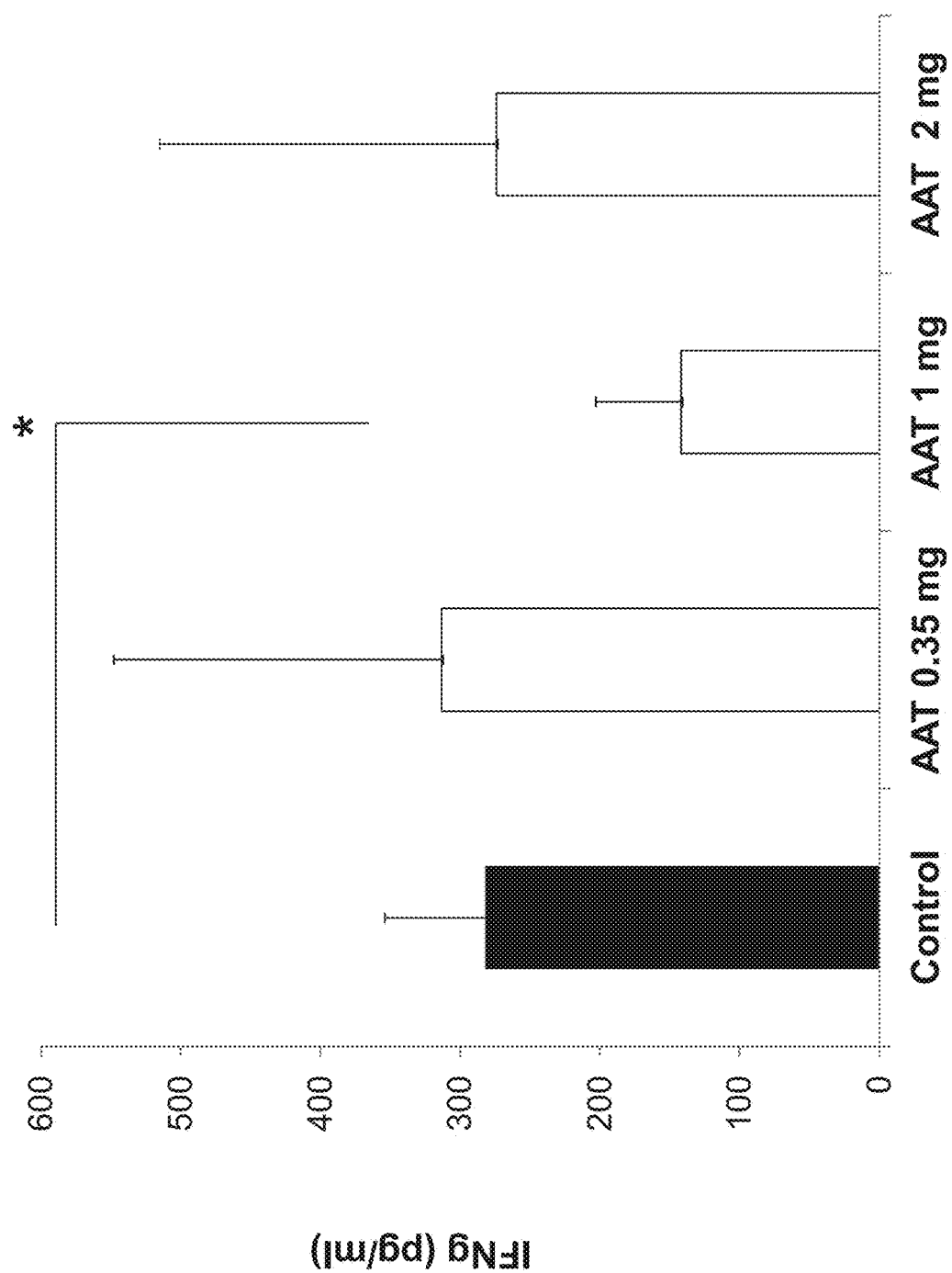

FIG. 3 is a graph demonstrating the effect of AAT treatment on IFNγ serum levels in the ConA-induced hepatitis mouse model, 15 hours following ConA administration.

Figure 4A:
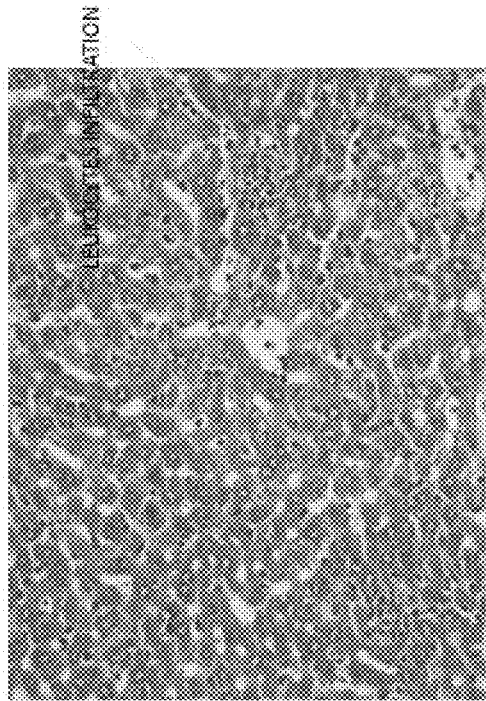
Figure 4B:
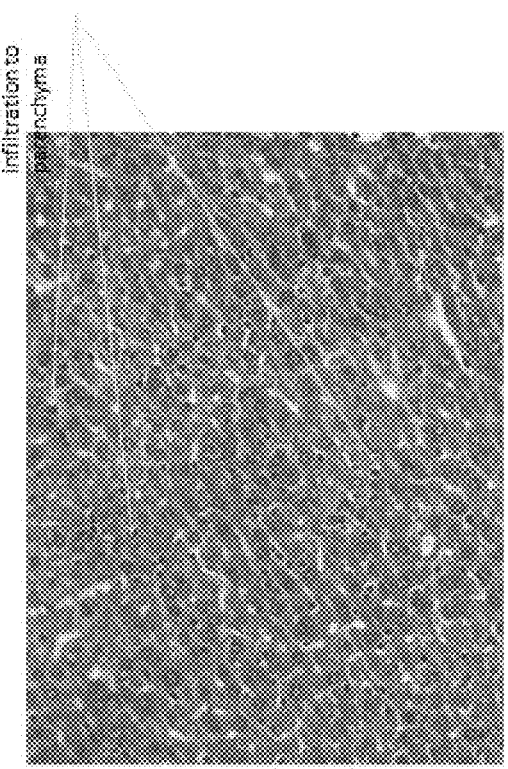

FIGS. 4A-B are representative histology pictures demonstrating the effect of AAT on lymphocyte infiltration in the ConA-induced hepatitis mouse model, 15 hours following ConA administration. FIG. 4A shows lymphocyte adhesion to veins and sinusoids, necrotic foci and leukocyte infiltration into the parenchyma in the control (DDW) mice. FIG. 4B shows reduced leukocyte infiltration into the parenchyma in the AAT-treated mice (0.35 mg/mouse).

Figure 5:
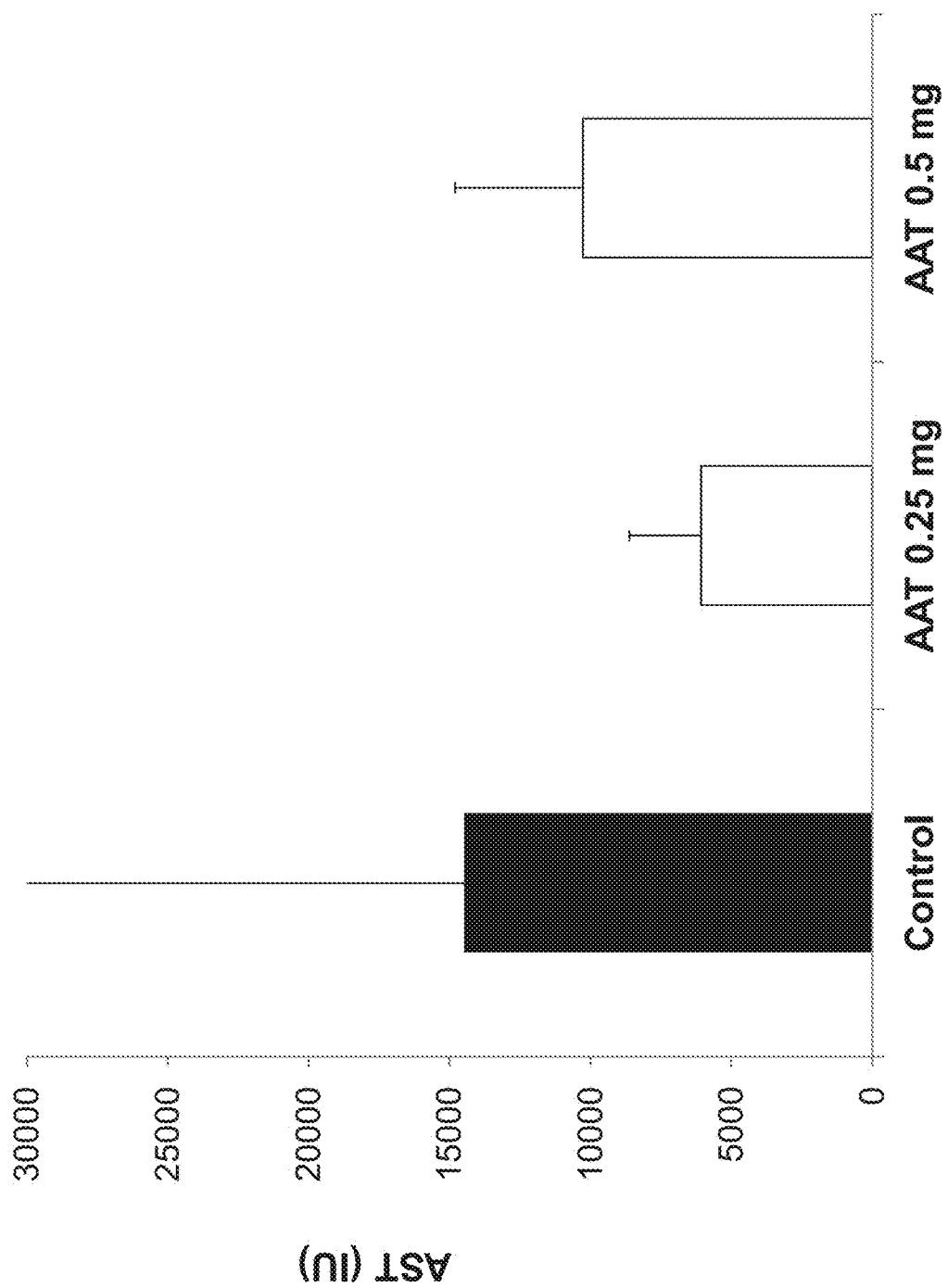

FIG. 5 is a graph of aspartate aminotransferase (AST) serum levels in control (DDW) and AAT-treated mice demonstrating the effect of AAT treatment on AST serum levels in the acetaminophen (APAP)-induced liver damage mouse model, 24 hours following APAP administration.

DESCRIPTION OF SPECIFIC EMBODIMENTS OF THE INVENTION

The present invention, in some embodiments thereof, relates to methods of treating liver diseases and, more particularly, but not exclusively, to the use of alpha-1 anti-trypsin (AAT) in the treatment of fatty liver disease and/or chronic liver rejection.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Alcoholic and non alcoholic fatty liver disease (also known as hepatosteatosis), is a prevalent liver condition that occurs when lipids accumulate in liver cells. The accumulation of lipids leads to cellular injury, sensitization of the liver to further injuries and damage to the hepatic microvascular circulation. Currently, there are no effective treatments for fatty liver disease (FLD).

Chronic liver transplant rejection is a process which occurs over time, typically several months to years following engraftment, even in the presence of successful immunosuppression. To date, there are no therapeutic regimens which can effectively inhibit the chronic liver rejection process.

Alpha-1 anti-trypsin (AAT) is a serine protease inhibitor (serpin) which inhibits a wide variety of proteases, primarily elastase, and protects the cells from proteolytic enzymes.

Whilst reducing the present invention to practice, the present inventors have now uncovered that treatment with AAT ameliorates levels of hepatic enzymes and inflammation in liver disorder models including models of FLD.

Specifically, as is illustrated hereinunder and in the Examples section, which follows, the present inventors have shown that administration of AAT induces a dose-dependent beneficial effect in the ConA hepatitis model as demonstrated by a reduction in the serum levels of liver enzymes and IFNγ and improved lymphocyte infiltration into the liver (Example 1, FIGS. 1A-C, 2, 3 and 4A-B and Table 1). Following, the present inventors have uncovered that administration of AAT alleviates acetaminophen (APAP)-induced toxicity in the APAP liver injury model as demonstrated by a reduction in the serum levels of liver enzymes (Example 2, FIG. 5). The inventors further demonstrate that administration of AAT ameliorated symptoms of fatty liver disease in the high fat diet (HFD) model (Example 3).

Thus, according to a first aspect of the present invention, there is provided a method of treating a liver disease selected form the group consisting of fatty liver disease and chronic liver rejection in a subject in need thereof, wherein said liver disease is not associated with genetic alpha-1 anti-trypsin (AAT) deficiency, the method comprising administering to the subject a therapeutically effective amount of AAT, thereby treating the liver disease in the subject.

According to another aspect of the present invention, there is provided an alpha-1 anti-trypsin (AAT) for use in treating a liver disease selected from the group consisting of fatty liver disease and chronic liver rejection, wherein said liver disease is not associated with genetic AAT deficiency.

As used herein, the terms "treating" and "treatment" refer to inhibiting or arresting the development of a pathology (disease, disorder or condition, e.g. fatty liver disease, chronic liver rejection) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein the term "subject" refers to a mammalian subject (e.g., human being) suffering from the pathology (e.g. fatty liver disease, chronic liver rejection). In a specific embodiment, this term encompasses individuals who are at risk to develop the condition. The subject may be of any gender or at any age including neonatal, infant, juvenile, adolescent, adult and elderly adult.

As used herein, the term "fatty liver disease (FLD)" refers to a liver disease caused by abnormal hepatic lipid deposits. FLD includes, but is not limited to, alcoholic fatty liver disease, nonalcoholic fatty liver disease and acute fatty liver of pregnancy.

Methods of FLD diagnosis and disease progression are known in the art and include, but are not limited to, clinical symptoms associated with FLD, serum levels of liver enzymes, non-invasive imaging techniques (e.g., ultrasonography, computed tomography, and magnetic resonance imaging), liver biopsy and histology.

Symptoms associated with FLD include e.g., abdominal discomfort (e.g., discomfort in the right upper abdominal quadrant), acanthosis nigricans, bowel dismotility, coma, constipation, disseminated intravascular coagulopathy, epigastric pain, fatigue, hepatomegaly (generally with a smooth, firm surface upon palpation), hypoglycemia, jaundice, lipomatosis, lipoatrophy, lipodystrophy, nausea, neurological defects, Palmer erythema, panniculitis, periumbilical pain, small bowel bacterial overgrowth, spider angiomata, splenomegaly, subacute liver failure, and vomiting.

Serum levels of liver enzymes such as e.g., alanine aminotransferase (ALT), aspartate aminotransferase (AST), γ-glutamyltransferase, alkaline phosphatase can be determined by any method known in the art.

According to specific embodiments, the fatty liver disease is an alcoholic fatty liver disease.

As used herein, the term "alcoholic fatty liver disease (AFLD)" refers to FLD resulting from a history of alcohol consumption and includes alcoholic hepatic steatosis (ASH) and alcoholic steatohepatitis.

According to specific embodiments, the fatty liver disease is a non-alcoholic fatty liver disease (NAFLD).

As used herein, the term "non-alcoholic fatty liver disease (NAFLD)" refers to FLD with no history of excessive alcohol consumption and includes hepatic steatosis and the more severe and advanced forms of non-alcoholic steatohepatitis (NASH), cirrhosis, hepatocellular carcinoma, and virus-induced (e.g., HIV, hepatitis).

According to specific embodiments, the fatty liver disease is a nonalcoholic steatohepatitis (NASH).

As used herein, the term "nonalcoholic steatohepatitis (NASH)" refers to NAFLD associated with inflammation, liver cell necrosis and fibrosis.

"Chronic liver rejection" typically refers to late rejection of the transplanted liver clinically developing 1 month to years' post transplant, generally characterized as failure of the organ after it has begun to perform its function in the recipient. Typically, chronic liver rejection is characterized by (1) progressive loss of interlobular and septal bile ducts; (2) increasing cholestasis manifested by increasing serum levels of alkaline phosphatase, gamma glutamyl transferase, and bilirubin; (3) obliterative arteriopathy, which leads to the loss of medium-sized arteries; and (4) ischemic damage to bile ducts, associated with a high incidence of graft failure.

Methods of chronic liver rejection diagnosis and disease progression are known in the art and include, but are not limited to, needle biopsy and histology, serum levels of liver enzymes, presence of anti-graft antibodies and non-invasive imaging techniques (e.g., CT scan, magnetic resonance imaging and angiography); and are disclosed e.g. in Wiesner et al. Liver Transplantation and Surgery, Vol 5, No 5 (September), 1999: pp 388-400; and Neumann et al. Graft 2002; 5: 102-107. According to specific embodiments, the transplanted liver is an orthotropic transplanted liver.

According to specific embodiments, the liver disease is not associated with a genetic AAT deficiency.

As used herein, the terms "genetic alpha-1 anti-trypsin deficiency" and "genetic AAT deficiency" refer to an autosomal co-dominant hereditary disorder in which a deficiency of AAT leads to a chronic uninhibited tissue breakdown. The disease is characterized by the degradation especially of lung tissue, eventually leading to characteristic manifestations of pulmonary emphysema or COPD. Genetic AAT deficiency can lead to various liver diseases in a minority of children and adults, including cirrhosis and liver failure, neonatal hepatitis and liver hepatocarcinoma.

According to specific embodiments, the liver disease is not associated with a disease selected from the group consisting of diabetes, obesity, hypertriglyceridemia, hypercholesterolemia and hypertension.

As used herein, the term "diabetes" refers to a metabolic disease characterized by abnormally high levels of glucose in the blood. The term may refer to type I diabetes, type II diabetes, gestational diabetes and latent autoimmune diabetes in adults (LADA).

As used herein, the term "obesity" refers to a medical condition in which there is an excess of body fat to the extent that it may have an adverse effect on health, leading to reduced life expectancy and/or increased health problems. According to specific embodiments, "obesity" refers to a condition whereby the subject has a BMI of ≥30 kg/m². According to specific embodiments, the obesity is abdominal obesity which is characterized by increased waist circumference.

As used herein, the term "hypertriglyceridemia" refers to a medical condition in which the level of blood triglycerides is chronically elevated as compared to the level that is generally accepted as normal or healthy by persons of ordinary skill in the art. According to specific embodiments, "hypertriglyceridemia" refers to a fasting blood triglyceride level of more than 150 mg/dL, more than 200 mg/dL, more than 400 mg/dL or more than 500 mg/dL.

As used herein, the term "hypercholesterolemia" refers to a medical condition in which the level of blood cholesterol is chronically elevated as compared to the level that is generally accepted as normal or healthy by persons of ordinary skill in the art. According to specific embodiments, "hypercholesterolemia" refers to fasting total cholesterol level of above 200 mg/dL above 240 mg/dL or above 300 mg/dL.

As used herein, the term "hypertension" refers to a medical condition in which the blood pressure in the arteries is chronically elevated above the accepted normal values for the age group and gender of the subject, and/or which is in a range considered to be associated with adverse health outcomes. According to specific embodiments, "hypertension" refers to a systolic blood pressure of greater than about 135 mm Hg and a diastolic blood pressure greater than 90 mm Hg.

As used herein the term "alpha 1 anti-trypsin (AAT)", EC Number 232-924-7, also known as Serpin Peptidase Inhibitor, Clade A, Member 1; Serine Proteinase Inhibitor, Clade A, Member 1Alpha-1 Protease Inhibitor; and Alpha-1-Antiproteinase refers to a polynucleotide and an expression product e.g. protein of the SERPINA1 gene. According to a specific embodiment, the AAT protein refers to the human protein, such as provided in the following GenBank Number NP_000286 (SEQ ID NO: 1). The AAT of the present invention is functional in treating FLD and/or chronic liver rejection. Methods of qualifying AAT for use in accordance with the present invention are well known in the art, some of which are described hereinabove and in the Examples section which follows and include e.g. a reduction in one or more symptoms or clinical manifestations of FLD and/or chronic liver rejection, a reduction in serum levels of a hepatic enzyme (e.g., ALT, AST, γ-glutamyltransferase, or alkaline phosphatase), a reduction in histological features of FLD e.g. cholestasis, fat cysts, fibrosis, granular iron, hepatocellular ballooning, number of leukocytes, inflammation, lobular disarray, lobular inflammation, macrovesicular steatosis, Mallory bodies, megamitochondria, necrosis, periodic acid-Schiff stained globules, portal inflammation, microvesicular steatosis, or steatosis, as determined by e.g. liver biopsies, and/or a reduction in histological features of chronic liver rejection e.g. bile ducts atrophy, lymphocytes in close contact to the degenerated bile duct cells, arteriopathy, lobular inflammation, eosinophilic transformation of biliary epithelial cytoplasm, nuclear enlargement and hyperchromasia, and ducts without complete lining by biliary epithelial cells.

As used herein, a reduction refers to a decrease of at least 1% in comparison to a suitable control e.g. in the absence or AAT on in the presence of a negative control peptide. According to specific embodiments, the decrease is in at least 10%, 20%, 30%, 40% or even higher say, 50%, 60%, 70%, 80%, 90% or more than 100%.

It should be noted that AAT inhibits the enzymatic activity of neutrophil elastase, cathespin G, proteinase 3, thrombin, trypsin, and chymotrypsin. Accordingly, an AAT suitable for use in accordance with some embodiments of the invention, inhibits the enzymatic activity of one or more of the aforementioned enzymes.

According to some embodiments of the invention AAT is a functional AAT homologue which exhibits the desired activity (i.e., treating FLD and/or chronic liver rejection). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptides set forth in SEQ ID NO: 1, or 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to human AAT as set forth in Gene Symbol SERPINA1, Gene ID: 5265 having the mRNA GenBank Accession Number NM_000295 (SEQ ID NO: 2). The homolog may also refer to an ortholog, a deletion, insertion, or substitution variant, including an amino acid substitution.

Sequence identity or homology can be determined using any protein or nucleic acid sequence alignment algorithm such as Blast, ClustalW, MUSCLE, and HHpred.

According to some embodiments of the invention, AAT is an AAT fragment, analog, mutant or derivative thereof, which is capable of treating FLD and/or chronic liver rejection, such as those disclosed for example in US Patent Application Publication No: US 20100111940.

A specific AAT mutant that can be used according to specific embodiments of the present invention is AZT, which is a misfolded but functionally active mutant of AAT (Burrows et al, Proc. Natl. Acad. Sci. USA 97:1796-1801, 2000.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |

TABLE 2-continued

| Non-conventional amino acid | Code | Non-conventional amino acid | Code |
| --- | --- | --- | --- |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having neuroprotective properties.

The peptides of some embodiments of the invention are preferably utilized in a linear form, although it will be appreciated that in cases where cyclization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

AAT can be purified from various plasma fractions as described e.g. in Feldman and Winkelman, Blood Separation and Plasma Fractionation, Wiley-Liss, Inc., pp. 341-383, 1991; Basis et al., Vopr. Med. Khim. 31:54-59, 1987; U.S. Pat. No. 6,974,792 and US Patent Application Publication No: US 20100111940, each of which is herein incorporated by reference in its entirety. AAT can also be produced in and purified from the milk of a non-human transgenic animal such as a cow as described e.g. in U.S. Pat. No. 6,194,553, the contents of which are fully incorporated herein by reference.

Alternatively, AAT is commercially available, for example, Aralast™ (Baxter), Zemaira™ (Aventis Behring), Prolastin™ (Talecris, N.C.), Prolastin C™ (Talecris, N.C.), Aerosolized AAT™ or Intravenous AAT™ (Kamada' Ltd. Israel).

Additionally or alternatively, the AAT of some embodiments of the invention may be synthesized by any techniques that are known to those skilled in the art of peptide synthesis, for example but not limited to recombinant DNA techniques (as described for example in Goeddel et al., Methods Enzymol. 185 (1990) 3-7; Wurm and Bernard, Curr. Opin. Biotechnol. 10 (1999) 156-159; Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463) or solid phase peptide synthesis (as described for example in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973; G. Schroder and K. Lupke, The Peptides, vol. 1, Academic Press (New York), 1965; and Andersson Biopolymers 2000; 55(3):227-50).

It should be noted that recombinantly produced AAT can exhibit varying post translational modifications (e.g. glycosylation) depending on the host cell type.

The present invention also contemplates administering to the subject a polynucleotide encoding AAT or one of the variants of AAT described hereinabove.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

Exemplary nucleic acid sequences encoding AAT which can be used in accordance with the present teachings include, but are not limited to SEQ ID NO: 2.

To express exogenous AAT in mammalian cells, the polynucleotide sequence encoding AAT is preferably ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this expression vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof. The regulatory sequences naturally associated with AAT can also be used. For example, one can incorporate a KpnI-KpnI fragment containing the promoter region, the first non-coding exon and the 5' portion of intron 1 of AAT (the sequence of which is given by Long et al., *Biochemistry* 23:4828, 1984).

According to a specific embodiment, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277].

In addition to the elements already described, the expression vector of some embodiments of the invention may contain enhancer elements, Polyadenylation sequences, eukaryotic replicon or other specialized elements.

Examples for mammalian expression vectors include, but are not limited to pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A⁺, pMTO10/A⁺, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Other than containing the necessary elements for the transcription and translation of the inserted coding sequence, the expression construct of some embodiments of the invention can also include sequences engineered to enhance stability, production, purification, yield or toxicity of the expressed peptide.

The AAT polynucleotide can be administered to the subject by any method known in the art including naked DNA, cell penetrating peptide or Viral and non-viral vectors (e.g. but not limited to liposomes, nanoparticles, mammalian vectors, virus-like particles, exosomes and the like). Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)].

The present invention also contemplates administering to the subject an agent that promotes activity of AAT. Thus, for example, an agent that promotes the activity of AAT may do so by increasing the secretion of AAT from a cell. 4-phenylbutyric acid (PBA) has been shown to elicit a marked increase in secretion of 1-AZT, a misfolded but functionally active mutant of α1-antitrypsin, in a model cell culture system (Burrows et al., *Proc. Natl. Acad. Sci. USA* 97:1796-1801, 2000). As PBA has been used safely in humans, it is an excellent candidate for inclusion in the present compositions and methods, and can be used regardless of the form of AAT.

The present invention also contemplates combination therapy comprising the AAT described herein with standard methods of treating FLD and/or chronic liver rejection, including, but not limited to metabolic modulators, antioxidants, immunomodulatory agents, immune-suppressive agents, anti-inflammatory agents, anti-microbial agents and anti-viral agents.

The AAT of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the AAT accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. AAT) effective to prevent, alleviate or ameliorate symptoms of a disorder (e.g., fatty liver disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide that the levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Typically used models for analyzing the effect of the agents described herein on FLD include but are not limited to genetic models such as the ob/ob mouse, fa/fa (Zucker) rat, or db/db mouse; overnutrition models, in which animals are fed, e.g., a high sucrose/fructose diet or a high fat diet; the methionine-choline diet deficiency model, which develops steatosis and in, some strains, fibrosis, a combination of high fat with methionine choline deficient diet; and transgenic models, such as mice that overexpress the transcription factor SREBP-1 that governs lipid synthesis. Other animal models are known in the art and are described in, e.g., Koteish et al., *Semin. Liver Dis* 21:89-104; (2001) Masuzaki et al., *Science*; (2001) 294:2166-2170 Lu et al., *Proc. Natl. Acad. Sci. U.S.A*; (2001) 98:5560-5565. Paterson et al., *Proc. Natl. Acad. Sci. U.S.A* 101:7088-7093; (2004) Farrell, "Animal models of steatosis" in *Fatty Liver Disease: NASH and Related Disorders*, Farrell et al., eds. Blackwell Publishing Ltd., Malden, Mass., 2005; Kirsch et al., *J. Gastroenter. Hepatol*; (2003) 18:1272-1282. Sahai et al., *Am. J. Physiol. Gastrointest. Liver Physiol:* 287.G1035-1043 (2004); and Lieber et al., *Am. J. Clin. Nutr.* (2004) 79:502-509

Typically used models for analyzing the effect of the agents described herein on chronic liver rejection include but are not limited to orthotopic allo- or xeno-liver transplantation mouse model such as disclosed e.g. in Qian et al. Transplant Proc. 1991 February; 23(1 Pt 1): 705-706; and Zhang et al. Transplantation. 1996 Nov. 15; 62(9):1267-72.

The doses shown in the Examples section which follows with respect to the mouse animal model can be converted for the treatment of other species such as human and other animals diagnosed with the liver disease. Conversion Table approved by the FDA is shown in Reagan-Shaw S., et al., FASEB J. 22:659-661 (2007)).

The human equivalent dose is calculated as follows: HED (mg/kg)=Animal dose (mg/kg) multiplied by (Animal $K_m$/human $K_m$).

According to some embodiments of the invention, the AAT is provided at an amount equivalent to a range of from about 12.5-50 mg/kg/day in mice, including any intermediate subranges and values therebetween.

According to specific embodiments, AAT is administered at a dose of 0.0001-5000 mg/kg, 0.0001-1000 mg/kg, 1-5000 mg/kg, 1-1000 mg/kg, 20-300 mg/kg, or 50-150 mg/kg, as disclosed e.g. in US Patent Application Publication Nos: US 20150010581 and US 20110237496.

According to specific embodiments, the AAT (e.g., of Aralast™, Prolastin™, or Zemaira™) is provided in an amount previously proven as safe and effective for other indications (the dosage of an AAT. Thus, for example, the recommended dosage of Aralast™ is 60 mg/kg body weight (e.g., 15-90 mg/kg), and it is typically administered once weekly by intravenous infusion at a rate that does not exceed 0.08 ml/kg body weight/minute (2.0 mg/kg body weight/minute).

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Animals—Male C57BL/6 mice (11-12 weeks old) were obtained from Harlan Laboratories (Jerusalem, Israel) and were maintained in the Animal Core of the Hadassah-Hebrew University Medical School. The mice received standard laboratory food and water ad libitum and were housed in a 12-hour light/dark cycle. All animal experiments were performed according to the guidelines and with the approval of the Hebrew University-Hadassah Institutional Committee for the Care and Use of Laboratory Animals.

Concanavalin A-induced hepatitis model—Concanavalin A (ConA, MP Biomedicals, USA) was dissolved in a solution consisting of 50 mM Tris pH 7, 150 mM NaCl, and 4 mM $CaCl_2$ and injected into the tail vein at a dose of 500 µg/mouse (15 mg/kg) in 250 µl. Mice were sacrificed 15 hours following ConA injection. Mice (n=5-6 mice per group) were administered orally or intraperitoneally (IP), as indicated, DDW (control); Dexamethasone (0.35 mg/mouse, control); or alpha-1 anti-trypsin (AAT, Sigma A-9024) at a dose of 0.2, 0.35, 1.0 or 2.0 mg per mouse, 2 hours prior ConA treatment.

Acetaminophen-mediated hepatotoxicity model—Acetaminophen (APAP)-mediated hepatotoxicity was induced in mice via oral administration of 4 mg APAP (Tiptipot, CST). Mice (n=5 mice per group) were administered IP DDW (control) or AAT at a dose of 0.25 or 0.5 mg per mouse, 2 hours following administration of APAP Assessment of Liver toxicity—Serum was obtained from individual mice at the indicated times and the levels of aspartate aminotransferase (AST) and alanine aminotransferase (ALT) were determined using a standard automated analyzer.

Cytokine measurement—Serum IFN-γ levels were measured at the indicated times in each animal using a commercially available ELISA kit (Quantikine, R&D Systems, MN, USA) according to manufacturer's instructions.

Histology—Mice were sacrificed at the indicated times and their livers were harvested. Paraffin-embedded liver sections were prepared from and sliced into 4-5 µm-thick sections and stained with hematoxylin-eosin (H&E). The sections were scored according to the extent of liver damage using a previously described method[13, 14] with the following parameters: lymphocyte adhesion to hepatic and portal veins and sinusoids, the number of infiltrating leukocytes into the liver parenchyma, and the number of necrotic lesions (all per 10× high-power field).

Statistical analysis—analysis was performed using Excel 2003 (Microsoft, Redmond, Wash., United States). The variables were expressed as mean±SD. The comparison of two independent groups was performed using Student's t-test. All tests applied were two-tailed. P value of 0.05 or less was considered to be statistically significant.

Example 1

Treatment with AAT Alleviates Immune-Mediated Liver Damage Induced by ConA In-Vivo The immunomodulatory effect of AAT on hepatitis model was assessed by determining liver toxicity in a ConA-induced hepatitis mouse model. As shown in FIGS. 1A-C, 2 and 3 and Table 1 hereinbelow, IP administration of AAT exerted a dose-dependent beneficial effect on this model. Statistically significant reduction in serum levels of the ALT liver enzyme was detected following treatment with AAT at doses of 0.35 and 1 mg per mouse groups (p<0.005), however treatment with AAT at a dose of 2 mg per mouse had no effect on ALT serum levels (FIGS. 1A-B). The AST levels corresponded to the ALT levels (FIG. 2). Interestingly, no effect on AST and ALT levels was observed when AAT was orally administered (FIGS. 1A-B and 2). A severe hepatitis can be defined by ALT levels of more the 1000 IU in the serum. AAT treatment at all doses tested reduced the number of mice developing severe disease, wherein a dose of 0.35 mg per mouse significantly reduced the number of mice developing severe disease to 50% as compared to 100% of the mice in the control (DDW) group (p<0.005, FIG. 1C).

AAT treatment also affected serum IFNγ levels; wherein a significant reduction in IFNγ levels was observed in mice treated IP with AAT at a dose of 1.0 mg per mouse (p<0.005), however no significant effect was evident by treatment with the low (0.35 mg per mouse) or high (2.0 mg per mouse) dosages (FIG. 3).

Table 1 below shows the effect of IP administration of AAT on liver damage as evaluated by histology. As evident, mice receiving an IP dose of 0.35 mg per mouse of AAT exhibited a significant improvement in the number of infiltrating leukocytes into the liver parenchyma. Representative sections from mice in the AAT-treated and control groups, demonstrating the decrease in cell infiltration among the hepatocytes are shown in FIGS. 4A-B.

TABLE 1

Histological score of liver damage in the ConA-induced hepatitis model (mean ± SD).

| Treatment | Lymphocyte adhesion (%) | Infiltrating leukocytes (%) | Necrotic lesions (%) |
|---|---|---|---|
| Control (DDW) | 2.53 ± 13 | 3.4 ± 8.5 | 0.98 ± 1.83 |
| Control (Dexamethasone) | 0.58 ± 2.5 | 0.58 ± 2.5 | 0 |
| AAT 0.35 mg/mouse IP | 2.8 ± 11.89 | 2.45 ± 8.33 | 1 ± 1.67 |

Example 2

Treatment with AAT Alleviates APAP-Mediated Liver Damage In-Vivo

The hepatoprotective effect of AAT was assessed by determining liver toxicity in a APAP-mediated liver damage mouse model. As shown in FIG. 5, IP administration of AAT at doses of 0.25 and 0.5 mg per mouse induced a decrease in serum levels of the AST liver enzyme as compared to the control (DDW) group. A similar effect on the serum ALT levels was also observed (data not shown).

Example 3

Treatment with AAT Alleviates Liver Damage in a Fatty Liver Model In-Vivo

The effect of AAT on fatty liver disease is assessed by determining liver toxicity in a high fat diet (HFD) with or without methionine choline deficient diet (MCD) mouse model.
Experimental Procedure:
Mice: 24 C57B1 mice, 12 weeks old.
Diet: MCD+HFD
Study goals: Determine the effect of AAT on non-alcoholic fatty liver disease (NAFLD) and nonalcoholic steatohepatitis (NASH):
  (i) Inflammatory signature:
  a. serum cytokines/adipokines
  b. Immune cells in spleen and liver
  (ii) Liver enzymes
  (iii) Liver histology
Experimental and Control Groups:

| Group | Treatment | Mode of administration once a week |
|---|---|---|
| A (N = 8) | Normal Saline (30 μl/mouse) | IV |
| B (N = 8) | 15 mg/kg AAT | IV |
| C (N = 8) | 150 mg/kg AAT | IV |

Blood is taken from the tail vein at the indicated time points and analyzed for:

| | Frequency |
|---|---|
| weight | Every 2 week |
| Liver enzymes | |
| ALT | Every 2 weeks |
| AST | |
| Inflammatory signature | |

Mice are sacrificed 14 weeks following beginning of treatment and analyzed for:
  Weight
  Epididymal fat weight (eq to visceral fat in humans)
  MRI—to look at steatosis
  ALT, AST
  Serum for cytokines-what cytokines: IL2, 6, 4, 5, 12, IFN (gamma), TNF and TGF. IL-10, il-4, il-13, mcp1,
  Adipokine—adiponectin which is anti-inflammatory adipokine and visfalatin
  CBC including eosinophils
  FACS for subsets of T cells
  Assessment of eotaxin levels in the liver and in the adipose tissue by mRNA
  Collect serum for Lipidomics to be conducted by OWL in Spain
  Collect serum for mRNA of lymphocytes, to be performed in the USA by Ilumina sequencing machines
  Liver fat quantification
  Liver biopsy followed by histological evaluation:
    1. H&E staining
    2. Fat staining (IHC): Oil-R-O (frozen sections)
      X2 non stained slides (paraffin embedded)
      Snap freeze −80, x3 samples (from each animal).
      Assessment of fibrosis based on staining Taken together, the data indicate that treatment with AAT exerts a hepatoprotective effect in ConA, APAP and HFD animal models.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Greene C M, Hassan T, Molloy K, et al. The role of proteases, endoplasmic reticulum stress and SERPINA1 heterozygosity in lung disease and alpha-1 anti-trypsin deficiency. Expert Rev Respir Med 2011; 5:395-411.
2. Hunt J M, Tuder R. Alpha 1 anti-trypsin: one protein, many functions. Curr Mol Med 2012; 12:827-35.

3. Guttman O, Baranovski B M, Schuster R, et al. Acute-phase protein alpha1-antitrypsin: diverting injurious innate and adaptive immune responses from non-authentic threats. Clin Exp Immunol 2014.
4. Bergin D A, Hurley K, McElvaney N G, et al. Alpha-1 antitrypsin: a potent anti-inflammatory and potential novel therapeutic agent. Arch Immunol Ther Exp (Warsz) 2012; 60:81-97.
5. Mizrahi M, Cal P, Rosenthal M, et al. Human alpha1-antitrypsin modifies B-lymphocyte responses during allograft transplantation. Immunology 2013; 140:362-73.
6. Shahaf G, Moser H, Ozeri E, et al. alpha-1-antitrypsin gene delivery reduces inflammation, increases T-regulatory cell population size and prevents islet allograft rejection. Mol Med 2011; 17:1000-11.
7. Tawara I, Sun Y, Lewis E C, et al. Alpha-1-antitrypsin monotherapy reduces graft-versus-host disease after experimental allogeneic bone marrow transplantation. Proc Natl Acad Sci USA 2012; 109:564-9.
8. Lewis E C, Mizrahi M, Toledano M, et al. alpha1-Antitrypsin monotherapy induces immune tolerance during islet allograft transplantation in mice. Proc Natl Acad Sci USA 2008; 105:16236-41.
9. Barnes T C, Cross A, Anderson M E, et al. Relative alpha(1)-anti-trypsin deficiency in systemic sclerosis. Rheumatology (Oxford) 2011; 50:1373-8.
10. Mota A, Sahebghadam Lotfi A, Jamshidi A R, et al. Alpha 1-antitrypsin activity is markedly decreased in Wegener's granulomatosis. Rheumatol Int 2014; 34:553-8.
11. Sun S, Fang K, Zhao Y, et al. Increased expression of alpha 1-anti-trypsin in the synovial tissues of patients with ankylosing spondylitis. Clin Exp Rheumatol 2012; 30:39-44.
12. Brunetti N D, Pellegrino P L, Correale M, et al. Acute phase proteins and systolic dysfunction in subjects with acute myocardial infarction. J Thromb Thrombolysis 2008; 26:196-202.
13. Margalit M, Ghazala S A, Alper R, et al. Glucocerebroside treatment ameliorates ConA hepatitis by inhibition of NKT lymphocytes. Am J Physiol Gastrointest Liver Physiol 2005; 289:G917-25.
14. Massaguer A, Perez-Del-Pulgar S, Engel P, et al. Concanavalin-A-induced liver injury is severely impaired in mice deficient in P-selectin. J Leukoc Biol 2002; 72:262-70.
15. Larson A M. Acetaminophen hepatotoxicity. Clin Liver Dis 2007; 11:525-48, vi.
16. McClain C J, Price S, Barve S, et al. Acetaminophen hepatotoxicity: An update. Curr Gastroenterol Rep 1999; 1:42-9.
17. Brodsky J L, Scott C M. Tipping the delicate balance: defining how proteasome maturation affects the degradation of a substrate for autophagy and endoplasmic reticulum associated degradation (ERAD). Autophagy 2007; 3:623-5.
18. Bashir M S, Jones D B, Wright D H. Alpha-1 anti-trypsin and CD30 expression occur in parallel in activated T cells. Clin Exp Immunol 1992; 88:543-7.
19. Ozeri E, Mizrahi M, Shahaf G, et al. alpha-1 antitrypsin promotes semimature, IL-10-producing and readily migrating tolerogenic dendritic cells. J Immunol 2012; 189:146-53.
20. Koulmanda M, Bhasin M, Awdeh Z, et al. The role of TNF-alpha in mice with type 1- and 2-diabetes. PLoS One 2012; 7:e33254.
21. Sandstrom C S, Ohlsson B, Melander O, et al. An association between Type 2 diabetes and alpha-antitrypsin deficiency. Diabet Med 2008; 25:1370-3.
22. Ochayon D E, Mizrahi M, Shahaf G, et al. Human alpha1-Antitrypsin Binds to Heat-Shock Protein gp96 and Protects from Endogenous gp96-Mediated Injury In vivo. Front Immunol 2013; 4:320.
23. Weir G C, Koulamnda M. Control of inflammation with alpha1-antitrypsin: a potential treatment for islet transplantation and new-onset type 1 diabetes. Curr Diab Rep 2009; 9:100-2.
24. Kaner Z, Ochayon D E, Shahaf G, et al. Acute Phase Protein alpha1-Antitrypsin Reduces Bacterial Burden in Mice by Selective Modulation of Innate Cell Responses. J Infect Dis 2014.

What is claimed is:

1. A method of treating nonalcoholic steatohepatitis (NASH) not associated with genetic alpha-1 anti-trypsin (AAT) deficiency in a subject in need thereof, the method comprising administering to the subject a therapeutically effective amount of a pharmaceutical composition comprising an active ingredient consisting of AAT as set forth in SEQ ID NO: 1, wherein said AAT inhibits the enzymatic activity of at least one enzyme selected from the group consisting of neutrophil elastase, cathespin G, proteinase 3, thrombin, trypsin and chymotrypsin, thereby treating the NASH in the subject.

2. The method of claim 1, wherein said subject does not have a disease selected from the group consisting of diabetes, obesity, hypertriglyceridemia, hypercholesterolemia and hypertension.

3. The method of claim 1, wherein said method further comprises administering to the subject a therapeutically effective amount of an antioxidant.

4. The method of claim 1, wherein said method further comprises administering to the subject a therapeutically effective amount of an immunomodulatory agent.

5. The method of claim 1, wherein said method further comprises administering to the subject a therapeutically effective amount of an immune-suppressive agent.

6. The method of claim 1, wherein said method further comprises administering to the subject a therapeutically effective amount of an anti-inflammatory agent.

7. The method of claim 1, wherein said method further comprises administering to the subject a therapeutically effective amount of an anti-microbial agent.

8. The method of claim 1, wherein said method further comprises administering to the subject a therapeutically effective amount of an anti-viral agent.

9. The method of claim 1, wherein said method consists of said administering said pharmaceutical composition comprising said AAT.

10. A method of treating nonalcoholic steatohepatitis (NASH) not associated with genetic alpha-1 anti-trypsin (AAT) deficiency in a subject in need thereof, the method comprising administering to the subject a therapeutically effective amount of AAT as set forth in SEQ ID NO: 1 and a therapeutically effective amount of an agent selected from the group consisting of an immunomodulatory agent, an immune-suppressive agent, an anti-inflammatory agent, anti-microbial agent and an anti-viral agent, wherein said AAT inhibits the enzymatic activity of at least one enzyme selected from the group consisting of neutrophil elastase, cathepsin G, proteinase 3, thrombin, trypsin and chymotrypsin, thereby treating NASH in the subject.

11. The method of claim 10, wherein said subject does not have a disease selected from the group consisting of diabetes, obesity, hypertriglyceridemia, hypercholesterolemia and hypertension.

12. The method of claim 10, wherein said subject does not have diabetes and obesity.

13. The method of claim 10, wherein said subject does not have diabetes or obesity.

14. The method of claim 1, wherein said subject does not have diabetes and obesity.

15. The method of claim 1, wherein said subject does not have diabetes or obesity.

* * * * *

SEQUENCE LISTING

```
<160> NUMBER OF SEQ ID NOS: 2

<210> SEQ ID NO 1
<211> LENGTH: 418
<212> TYPE: PRT
<213> ORGANISM: Homo sapiens

<400> SEQUENCE: 1

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95
```

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 2
<211> LENGTH: 3220
<212> TYPE: DNA
<213> ORGANISM: Homo sapiens

<400> SEQUENCE: 2
acaatgactc ctttcggtaa gtgcagtgga agctgtacac tgcccaggca aagcgtccgg    60
gcagcgtagg cgggcgactc agatcccagc cagtggactt agccctgtt tgctcctccg    120 ataactgggg tgaccttggt taatattcac cagcagcctc cccgttgcc cctctggatc    180 cactgcttaa atacggacga ggacagggcc ctgtctcctc agcttcaggc accaccactg    240

```
acctgggaca gtgaatcgac aatgccgtct tctgtctcgt ggggcatcct cctgctggca    300
ggcctgtgct gcctggtccc tgtctccctg gctgaggatc cccagggaga tgctgcccag    360
aagacagata catcccacca tgatcaggat cacccaacct tcaacaagat caccccccaac   420
ctggctgagt tcgccttcag cctataccgc cagctggcac accagtccaa cagcaccaat    480
atcttcttct ccccagtgag catcgctaca gcctttgcaa tgctctccct ggggaccaag    540
gctgacactc acgatgaaat cctggagggc tgaatttca acctcacgga gattccggag     600
gctcagatcc atgaaggctt ccaggaactc ctccgtaccc tcaaccagcc agacagccag    660
ctccagctga ccaccggcaa tggcctgttc tcagcgagg gcctgaagct agtggataag     720
ttttggagg atgttaaaaa gttgtaccac tcagaagcct tcactgtcaa cttcggggac     780
accgaagagg ccaagaaaca gatcaacgat tacgtggaga agggtactca agggaaaatt    840
gtggatttgg tcaaggagct tgacagagac acagttttttg ctctggtgaa ttacatcttc   900
tttaaaggca atgggagag acctttgaa gtcaaggaca ccgaggaaga ggacttccac      960
gtggaccagg tgaccaccgt gaaggtgcct atgatgaagc gtttaggcat gtttaacatc   1020
cagcactgta agaagctgtc cagctgggtg ctgctgatga aatacctggg caatgccacc   1080
gccatcttct tcctgcctga tgaggggaaa ctacagcacc tggaaaatga actcacccac   1140
gatatcatca ccaagttcct ggaaaatgaa gacagaaggt ctgccagctt acatttaccc   1200
aaactgtcca ttactggaac ctatgatctg aagagcgtcc tgggtcaact gggcatcact   1260
aaggtcttca gcaatggggc tgacctctcc ggggtcacag aggaggcacc cctgaagctc   1320
tccaaggccg tgcataaggc tgtgctgacc atcgacgaga agggactga agctgctggg    1380
gccatgtttt tagaggccat acccatgtct atcccccccg aggtcaagtt caacaaaccc   1440
tttgtcttct taatgattga acaaaatacc aagtctcccc tcttcatggg aaaagtggtg   1500
aatcccaccc aaaaataact gcctctcgct cctcaaccc tcccctccat ccctggcccc    1560
ctccctggat gacattaaag aagggttgag ctggtccctg cctgcatgtg actgtaaatc   1620
cctcccatgt tttctctgag tctcccttttg cctgctgagg ctgtatgtgg gctccaggta   1680
acagtgctgt cttcgggccc cctgaactgt gttcatggag catctggctg ggtaggcaca   1740
tgctgggctt gaatccaggg gggactgaat cctcagctta cggacctggg cccatctgtt   1800
tctggagggc tccagtcttc cttgtcctgt cttggagtcc caagaagga atcacagggg    1860
aggaaccaga taccagccat gaccccaggc tccaccaagc atcttcatgt cccctgctc    1920
atccccact cccccccacc cagagttgct catcctgcca gggctggctg tgcccacccc    1980
aaggctgccc tcctgggggc cccagaactg cctgatcgtg ccgtggccca gttttgtggc   2040
atctgcagca acacaagaga aggacaatg tcctcctctt gacccgctgt cacctaacca    2100
gactcgggcc ctgcacctct caggcacttc tggaaaatga ctgaggcaga ttcttcctga   2160
agcccattct ccatggggca acaaggacac ctattctgtc cttgtccttc catcgctgcc   2220
ccagaaagcc tcacatatct ccgtttagaa tcaggtccct tctccccaga tgaagaggag   2280
ggtctctgct ttgttttctc tatctcctcc tcagacttga ccaggcccag caggccccag   2340
aagaccatta ccctatatcc cttctcctcc ctagtcacat ggccataggc ctgctgatgg   2400
ctcaggaagg ccattgcaag gactcctcag ctatgggaga ggaagcacat cacccattga   2460
cccccgcaac ccctccctttt cctcctctga gtcccgactg gggccacatg cagcctgact   2520
tctttgtgcc tgttgctgtc cctgcagtct tcagagggcc accgcagctc cagtgccacg   2580
gcaggaggct gttcctgaat agccctgtg gtaagggcca ggagagtcct tccatcctcc    2640
```

```
aaggccctgc taaaggacac agcagccagg aagtcccctg ggcccctagc tgaaggacag    2700
cctgctccct ccgtctctac caggaatggc cttgtcctat ggaaggcact gccccatccc    2760
aaactaatct aggaatcact gtctaaccac tcactgtcat gaatgtgtac ttaaaggatg    2820
aggttgagtc ataccaaata gtgatttcga tagttcaaaa tggtgaaatt agcaattcta    2880
catgattcag tctaatcaat ggataccgac tgtttcccac acaagtctcc tgttctctta    2940
agcttactca ctgacagcct ttcactctcc acaaatacat taaagatatg gccatcacca    3000 agcccctag gatgacacca gacctgagag tctgaagacc tggatccaag ttctgactttt    3060 tccccctgac agctgtgtga ccttcgtgaa gtcgccaaac ctctctgagc cccagtcatt    3120
gctagtaaga cctgcctttg agttggtatg atgttcaagt tagataacaa aatgtttata    3180
cccattagaa cagagaataa atagaactac atttcttgca                         3220
```